United States Patent [19]

Aki et al.

[11] Patent Number: 4,966,796

[45] Date of Patent: Oct. 30, 1990

[54] GRAINS-STORING BAG

[75] Inventors: Seietsu Aki, Osaka; Goro Shinjo, Toyonaka, both of Japan

[73] Assignee: Sumitomo Chemical Company, Limited, Osaka, Japan

[21] Appl. No.: 335,364

[22] Filed: Apr. 10, 1989

[30] Foreign Application Priority Data

Apr. 15, 1988 [JP] Japan .................................. 63-94095

[51] Int. Cl.$^5$ ...................... B65D 30/02; A01N 25/34
[52] U.S. Cl. ................................... 428/34.3; 424/415; 424/DIG. 10; 428/907; 493/210; 493/186
[58] Field of Search ............... 428/907, 34.3; 424/415, 424/DIG. 10; 53/172; 493/210, 186

[56] References Cited

U.S. PATENT DOCUMENTS

| | | | |
|---|---|---|---|
| 3,106,567 | 10/1963 | Hawthorne et al. | 424/415 |
| 3,993,782 | 11/1976 | Jurd | 514/736 |
| 4,234,582 | 11/1980 | Takahashi et al. | 514/241 |
| 4,352,833 | 10/1982 | Young et al. | 428/907 |
| 4,533,435 | 8/1985 | Intili | 428/907 |
| 4,576,801 | 3/1986 | Parry et al. | 424/415 |
| 4,631,231 | 12/1986 | Stendel et al. | 428/907 |

FOREIGN PATENT DOCUMENTS 0028771  2/1982  Japan ..................... 424/415

*Primary Examiner*—James Seidleck
*Attorney, Agent, or Firm*—Stevens, Davis, Miller & Mosher

[57] ABSTRACT

A bag for protecting grains from insect pests harmful to stored grains is produced by treating one piece of kraft paper with an insecticidal solution containing a pyrethroide insecticide, laminating 1 to 5 pieces of kraft paper, to which the pyrethroidal insecticidal compound is not applied, onto the insecticidally unprocessed surface of the former kraft paper, and then forming the resulting kraft paper laminate into a bag so that the surface, to which the pyrethroid insecticide has been applied, of the former kraft paper faces the outside. When grains are preserved in the bag according to the present invention, the grains can effectively be protected from insect pests harmful to stored grains.

8 Claims, No Drawings

GRAINS-STORING BAG

The present invention relates to a method for protecting grains from insect pests harmful to stored grains (hereinafter referred simply to as the insect pests) during the preservation of grains.

Hitherto, for preventing the insect pests from damaging grains, there have been known such methods as fumigation-in-warehouse with chloropicrin, methyl bromide, organo-phosphorus insecticides, pyrethroid insecticides, etc., and spraying of active ingredients in the form of wettable powders, emulsifiable concentrates, oil sprays, etc. onto grains. With regard to insect pests-controlling bags applied with chemicals, JP-A-57-28771 discloses those in which d-allethrin is used as the insecticidally active ingredient.

These methods, however, have problems that the activity against insect pests is insufficient, and that grains are contaminated by the active ingredient and it is taken as a food into human bodies and animal bodies. Further, there is also a problem that the activity does not last for a long period of time. These methods, therefore, may not always be said to be satisfactory.

In view of the situation, the present inventors have made an extensive study, and as a result, have found that grains can be protected from the insect pests over a long period of time by forming a multi-layer kraft paper into a bag, which paper had previously treated with an insecticidal solution containing a certain kind of pyrethroid insecticides and preserving grains in the bag and can be prevented from contaminating grains by the insecticides. The present inventors thus attained to the present invention.

According to the present invention, there are provided:

(1) a method for protecting grains from the insect pests (hereinafter referred to as the present method) which comprises preserving grains in a bag which had been produced by treating one side of a kraft paper with an insecticidal solution containing at least one member selected from the group consisting of the following pyrethroid insecticides;

3-phenoxybenzyl chrysanthemate,
3-phenoxybenzyl 3-(2,2-dichlorovinyl)-2,2-dimethylcyclopropanecarboxylate,
α-cyano-3-phenoxybenzyl chrysanthemate,
5-benzyl-3-furylmethyl chrysanthemate,
α-cyano-3-phenoxybenzyl 2-(4-chlorophenyl)-3-methylbutyrate,
α-cyano-3-phenoxybenzyl 2,2,3,3-tetramethylcyclopropanecarboxylate,
α-cyano-3-phenoxybenzyl 3-(2,2-dichlorovinyl)-2,2-dimethylcyclopropanecarboxylate,
α-cyano-3-phenoxybenzyl 3-(2,2-dibromovinyl)-2,2-dimethylcyclopropanecarboxylate,
α-cyano-3-phenoxybenzyl 3-(2-chloro-3,3,3-trifluoro-1-propenyl)-2,2-dimethylcyclopropanecarboxylate,
α-cyano-3-phenoxybenzyl 2-(4-difluoromethoxyphenyl)-3-methylbutyrate,
α-cyano-4-fluoro-3-phenoxybenzyl 3-(2,2-dichlorovinyl)-2,2-dimethylcyclopropanecarboxylate,
2-(4-ethoxyphenyl)-2-methylpropyl 3-phenoxybenzyl ether and
α-cyano-3-phenoxybenzyl 2,2-dimethyl-3-(1,2,2,2-tetrabromoethyl)cyclopropanecarboxylate, laminating one to five pieces of insecticidally unprocessed kraft paper onto the unprocessed side of the above-processed paper, and forming the resulting multi-layer kraft paper laminate into a bag so that the insecticidally processed surface faces the outside, and (2) a bag for protecting grains from the insect pests (hereinafter referred to as the present bag) which is produced by treating one side of a kraft paper with the foregoing insecticidal solution, optionally with the aid of a solvent, laminating one to five pieces of an insecticidally unprocessed kraft paper onto the unprocessed side of the above-processed paper, and forming the resulting multi-layer kraft paper laminate into a bag so that the insecticidally processed surface faces the outside.

For treating a kraft paper with the pyrethroids mentioned above, there is usually utilized a method such as absorption processing method and the like, in which the surface of kraft paper is treated with insecticidal solution. The absorption processing method utilized in the present invention comprises, for example, formulating at least one pyrethoroid mentioned above into an insecticidal solution (e.g. oil sprays, emulsifiable concentrates, water-based emulsifiable concentrates, flowable concentrates) with a known formulation process, uniformly diluting the insecticidal solution with a solvent such as water, 1,1,1-trichloroethane, methylene chloride, kerosene, etc., and applying the resulting dilute solution by (1) treating the surface of a kraft paper with the solution, (2) dipping a kraft paper into the solution for 0.1 minute to 1 hour, (3) spraying the solution onto a kraft paper with an air sprayer or air gun with the aid of compressed air, or (4) passing a kraft paper through vertically-arranged two rotating rollers, one of which is dipped in the solution, to apply a prescribed amount of the solution to one side of the kraft paper.

The kraft paper used in the present invention includes non-bleached kraft paper, semi-bleached kraft paper and bleached kraft paper, etc. Further, usually used water-proof processing, etc. may be applied in order to prevent moisture permeation.

The amount of the insecticidal solution applied to the kraft paper is not critical and varies with the kind of the foregoing pyrethroids and combination thereof. Usually, the amount is 10 to 1,250 mg, as the active ingredient, per square meter of the kraft paper. In the case the insecticidal solution is applied, diluted with a solvent if necessary, to the surface of the kraft paper the oil spray, emulsifiable concentrate, water-based emulsifiable concentrate or flowable concentrate as it is or diluted with a solvent about 1–1000 times so as to contain the pyrethroid insecticide in an amount of 0.1–90% by weight, preferably 5–50% by weight, may be coated onto the kraft paper at a rate of 50 to 1,000 ml/m². In the case a kraft paper is dipped in the insecticidal solution, a dilute solution of the same concentration and dilution rate as described above may be prepared, and the kraft paper may be dipped therein. In the case the insecticidal solution is sprayed onto the kraft paper, a dilute solution prepared at the same concentration and dilution rate as described above may be sprayed thereon. The same applies to the case the kraft paper is passed between vertically arranged two rotating rollers, one of which is dipped in the insecticidal solution, to apply the solution to one side of the kraft paper.

Table 1 shows some pyrethroids which can be used in the present invention.

TABLE 1

| Compound No. | General name | Chemical name |
|---|---|---|
| (1) | d-Phenothrin | 3-phenoxybenzyl (1R)-cis.trans-chrysanthemate |
| (2) | Permethrin | 3-phenoxybenzyl d,1-cis.trans-3-(2,2-dichlorovinyl)-2,2-dimethylcyclopropanecarboxylate |
| (3) | Cyphenothrin | α-cyano-3-phenoxybenzyl (1R)-cis.trans-chrysanthemate |
| (4) | Resmethrin | 5-benzyl-3-furylmethyl (1R)-cis.trans-chrysanthemate |
| (5) | Fenvalerate | α-cyano-3-phenoxybenzyl 2-(4-chlorophenyl)-3-methylbutyrate |
| (6) | Fenpropathrin | α-cyano-3-phenoxybenzyl 2,2,3,3-tetramethylcyclopropanecarboxylate |
| (7) | Cypermethrin | α-cyano-3-phenoxybenzyl d,1-cis.trans-3-(2,2-dichlorovinyl)-2,2-dimethylcyclopropanecarboxylate |
| (8) | Deltamethrin | (S)-α-cyano-3-phenoxybenzyl (1R,3R)-3-(2,2-dibromovinyl)-2,2-dimethylcyclopropanecarboxylate |
| (9) | Cyhalothrin | α-cyano-3-phenoxybenzyl (Z)-(1RS,3RS)-3-(2-chloro-3,3,3-trifluoro-1-propenyl)-2,2-dimethylcyclopropanecarboxylate |
| (10) | Flucythrinate | (RS)-α-cyano-3-phenoxybenzyl (S)-2-(4-difluoromethoxyphenyl)-3-methylbutyrate |
| (11) | Cyfluthrin | α-cyano-4-fluoro-3-phenoxybenzyl 3-(2,2-dichlorovinyl)-2,2-dimethylcyclopropanecarboxylate |
| (12) | Ethofenprox | 2-(4-ethoxyphenyl)-2-methylpropyl 3-phenoxybenzyl ether |
| (13) | Tralomethrin | (S)-α-cyano-3-phenoxybenzyl (1R,3S)-2,2-dimethyl-3-(1,2,2,2-tetrabromoethyl)-cyclopropanecarboxylate |

The pyrethroids are not limited to the compounds shown in Table 1, and they include the optical and geometical isomers thereof and the mixtures thereof. Any of those exhibiting a high lethal activity against the insect pests may be used. Also, synergists such as piperonyl butoxide, isobornyl thiocyanatoacetate, lethane, S-421, etc. may be used in combination with the insecticides.

For forming the multi-layer kraft paper laminate into a bag for protecting grains from the insect pests, it is sufficient to utilize a usually used method for packing grains, cements, fertilizers, etc.

The size of the present bag can be changed depending upon the uses. Usually, however, it can be prepared by pasting one or more pieces of kraft paper to form into a cylindrical tube, sewing the top and bottom of the tube closing with a strong thread such as the so-called Komekuchiito (a hemp thread usually used for closing rice-storing bags), strings used for closing grain-storing bags etc. to form into a bag of 65–80 cm in length and 40–50 cm in width.

For the purpose of moisture-proof processing, a polymer film such as a thin polyethylene or polypropylene film of about 10 to about 1,000 μm thick may be inserted between the intermediate layers of the multi-layer kraft paper laminate or may back the inner surface thereof.

The pyrethroids used in the present invention are formulated into oil sprays, emulsifiable concentrates, water-based emulsifiable concentrates or flowable concentrates. A carrier used in the formulation includes for example water, alcohols (e.g. methanol, ethanol, glycerin, polyethylene glycol), ethers (e.g. tetrahydrofuran, dioxane), aliphatic hydrocarbons (e.g. hexane, kerosene, paraffin, petroleum benzine), esters (e.g. ethyl acetate), etc.

Into the liquid formulations may further be incorporated the usual emulsifiers, dispersing agents, spreading.wetting agents, suspending agents, preservatives, propellants, etc. Further, the usual film-forming agents may be incorporated thereinto.

Specific examples of the above agents are for example soaps; polyoxyethylene fatty alcohol ethers such as polyoxyethylene oleyl ether, etc.; polyoxyethylene alkylaryl ethers such as polyoxyethylene nonylphenyl ether, etc.; emulsifiers such as polyoxyethylene fatty acid esters, fatty acid glycerides, sorbitan fatty acid esters, surfuric acid esters of higher alcohols, alkylarylsulfonates (e.g. sodium dodecylbenzenesulfonate), etc.; spreading.wetting agents such as glycerin, polyethylene glycol, etc.; suspending agents such as casein, gelatin, alginic acid, carboxymethyl cellulose, gum arabic, hydroxypropyl cellulose, bentonite, etc.; preservatives such as methyl p-oxybenzoate, ethyl p-oxybenzoate, propyl p-oxybenzoate, butyl p-oxybenzoate, etc.; propellants such as dimethyl ether, chlorofluorocarbon, carbon dioxide gas, etc.; cellulose derivatives such as nitrocellulose, acetylcellulose, acetylbutyrylcellulose, methyl cellulose, etc.; vinyl resins such as vinyl acetate resins, etc.; and various film.-forming agents such as polyvinyl alcohol, etc.

In order to improve the storage stability of the kraft paper treated with the insecticidal solution, antioxidants such as tert-butylhydroquinone, n-propyl gallate, 3-tert-butyl-4-hydroxyanisole, butylated hydroxytoluene, etc. may be incorporated.

The insect pests which can be controlled by the present invention include insect pests belonging to Silvanidae such as saw-toothed grain beetle (*Oryzaephilus surinamensis*), merchant grain beetle (*Oryzaephilus mercator*), etc.; insect pests belonging to Cucujidae such as flat grain beetle (*Cryptolestes pusillus*), rustred grain beetle (*Cryptolestes ferrugineus*), etc.; insect pests belonging to Tenebrionidae such as red flour beetle (*Tribolium castaneum*), confused flour beetle (*Tribolium confusum*), dark mealworm beetle (*Tenebrio obscurus*), yellow mealworm beetle (*Tenebrio molitor*), lesser mealworm beetle (*Alphitobius diaperinus*), *Palembus dermestoides*, etc.; insect pests belonging to Trogositidae such as bread beetle (*Tenebroides mauritanicus*), etc.; insect pests belonging to Rhynchophoridae such as maize weevil (*Sitophilus zeamais*), rice weevil (*Sitophilus oryzae*), etc.; insect pests belonging to Dermestidae such as hide beetle (*Dermestes maculatus*), black larder beetle (*Dermestes ater*), etc.; insect pests belonging to Anobiidae such as biscuit beetle (*Stegobium paniceum*), cigarette beetle (*Lasioderma serricorne*), etc.; insect pests belonging to Ptinidae such as *Ptinus japonicus, Gibbium aequinoctiale*, etc., insect pests belonging to Bruchidae such as four-spotted bean weevil (*Callosobruchus maculatus*), azuki bean weevil (*Callosobruchus chinensis*), bean weevil (*Acanthoscelides obtectus*), pea weevil (*Brunchus pisorum*), broadbean weevil (*Bruchus rufima-*

*nus*), etc.; insect pests belonging to Tineidae such as European grain moth (*Nemapogon granellus*), etc.; insect pests belonging to Pyralidae such as Mediterranean flour moth (*Anagasta kuehniella*), almond moth (*Ephestia cautella*), Indian meal moth (*Plodia interpunctella*), etc.; insect pests belonging to Gelechiidae such as Angoumois grain moth (*Sitotroga cerealella*), etc.; and insect pests belonging to PSOCOPTERA such as *Liposcelis bostrychophilus*, etc.

Grains to be protected by the present invention include gramineous crops such as rice, wheat, barley, rye, sawa millet, oats, German millet, millet, corn, etc., and pulse such as peas, kidney beans, broad beans, soybeans, etc. Further, the powdery products of these crops and pulse are also included in the grains to be protected by the present invention.

The present invention will be illustrated in more detail with reference to the following examples, but it is not limited to these examples.

EXAMPLE 1

Twenty parts of the present compound (2) was dissolved in 70 parts of xylene with the aid of 10 parts of Sorpol 1200K ® (produced by Toho Kagaku Kogyo Co., Ltd.) to prepare an emulsion. Then, the emulsion was diluted 20 times with water. A kraft paper was dipped in the resulting aqueous solution for about 30 seconds and air-dried. Three pieces of untreated kraft paper were laminated on the treated paper to prepare a four-layer kraft paper laminate. The laminate was formed into a bag for protecting grains from the insect pests of 80 cm in height and 50 cm in width having the treated paper as the outermost layer. Further, moisture-proof bags for protecting grains from the insect pests were obtained by inserting a thin polymer film between the intermediate layers of the four-layer kraft paper laminate or by backing the inner surface of the laminate with the film, followed by forming the resulting laminate into a bag in the same manner as above.

EXAMPLE 2

200 Grams of the compound (2) was added to 400 g of a 15 wt. % aqueous solution of Gosenol GL-05 (polyvinyl alcohol, produced by Nippon Synthetic Chemical Industry Co., Ltd.). Then, the resulting mixture was stirred at room temperature (about 20° C.) by means of T. K. Homomixer (trade name of Tokushu Kika Kogyo Co., Ltd.) for 5 minutes at a rate of 700 rpm to obtain a dispersion. To this dispersion were successively added 0.5 wt. % of xanthane gum, 400 g of a 1.0 wt. % aqueous solution of aluminum magnesium silicate and 100 g of propylene glycol. The mixture was mixed for several minutes with mild stirring to obtain a flowable concentrate having an active ingredient concentration of 10 wt. %.

This flowable concentrate was diluted ten times with water.

A kraft paper was dipped in said aqueous solution for about 30 seconds and air-dried. Three pieces of untreated kraft paper were laminated on this treated paper. The resulting laminate was formed into a bag for protecting grains from insect pests of 80 cm in height and 50 cm in width having the treated paper as the outermost layer.

EXAMPLE 3

The test compounds (1) to (12) were each diluted with acetone to a prescribed concentration. 2 Milliliters of each dilute solution was uniformly dropped onto a kraft paper of 15 cm square and air-dried. After the kraft paper had been stored for 2, 4, 8 and 16 weeks at room temperature in a dark place, three pieces of a glass ring of 4 cm in diameter and 2 cm in height were put on the treated paper. Then, ten adults of cigarette beetle (*Lasioderma serricorne*) were released in the rings. Twenty-four hours after the release, the percentages of dead and moribund insects at a dosage rate of the test compound of 250 or 1,250 mg per square meter of the paper were determined. The percentage of dead and moribund insects (%) was calculated by the following equation.

$$\text{Percentage of dead and moribund insects (\%)} = \frac{\text{Number of dead and moribund insects}}{\text{total number of test insects}} \times 100$$

The results are shown in Table 2.

TABLE 2

| | Percentage of dead and moribund insects (%) | | | | | | | |
|---|---|---|---|---|---|---|---|---|
| | 2 | | 4 | | 8 | | 16 (weeks) | |
| Test compound | 250 mg/m$^2$ | 1250 mg/m$^2$ | 250 mg/m$^2$ | 1250 mg/m$^2$ | 250 mg/m$^2$ | 1250 mg/m$^2$ | 250 mg/m$^2$ | 1250 mg/m$^2$ |
| (1) | 100 | 100 | 100 | 100 | 100 | 100 | 100 | 100 |
| (2) | 100 | 100 | 100 | 100 | 100 | 100 | 100 | 100 |
| (3) | 100 | 100 | 100 | 100 | 48 | 100 | 10 | 100 |
| (4) | 100 | 100 | 100 | 100 | 88 | 100 | 65 | 100 |
| (5) | 100 | 100 | 100 | 100 | 100 | 100 | 100 | 100 |
| (6) | 100 | 100 | 100 | 100 | 100 | 100 | 100 | 100 |
| (7) | 100 | 100 | 100 | 100 | 100 | 100 | 100 | 100 |
| (8) | 100 | 100 | 100 | 100 | 100 | 100 | 100 | 100 |
| (9) | 100 | 100 | 100 | 100 | 100 | 100 | 100 | 100 |
| (10) | 100 | 100 | 100 | 100 | 100 | 100 | 100 | 100 |
| (11) | 100 | 100 | 100 | 100 | 100 | 100 | 100 | 100 |
| (12) | 100 | 100 | 100 | 100 | 100 | 100 | 100 | 100 |

EXAMPLE 4

The test compounds (2), (5), (6), (8), (12) and (13) were each diluted with acetone to a prescribed concentration. Then, 2 ml of the dilute solution was uniformly dropped onto a kraft paper of 15 cm square and air-dried. After the paper had been stored for 3, 12 and 24 weeks at a temperature of 25° C. in a dark place, three pieces of a glass ring of 4 cm in diameter and 2 cm in height were put on the paper. Then, ten adults of red flour beetle (*Tribolium castaneum*) were released in the rings. Twenty-four hours after the release, the percentages of dead and moribund insects at a dosage rate of the test compound of 125, 250, 500 or 1,000 mg per square meter of the paper were determined. The percentage of dead and moribund insects (%) was calculated by the same manner as in Example 3.

The results are shown in Table 3.

TABLE 3

| Test compound | Dosage rate (mg/m²) | Percentage of dead and moribund insects (%) (at 25° C., in dark place) | | |
|---|---|---|---|---|
| | | 3 | 12 | 24 (weeks) |
| (2) | 125 | 82 | 95 | 37 |
| | 250 | 75 | 80 | 67 |
| | 500 | 97 | 95 | 97 |
| | 1000 | 97 | 97 | 95 |
| (5) | 125 | 98 | 100 | 72 |
| | 250 | 100 | 94 | 90 |
| | 500 | 100 | 100 | 95 |
| | 1000 | 100 | 100 | 100 |
| (6) | 125 | 96 | 95 | 70 |
| | 250 | 100 | 88 | 82 |
| | 500 | 100 | 100 | 100 |
| | 1000 | 100 | 100 | 100 |
| (8) | 125 | 90 | 98 | 90 |
| | 250 | 100 | 100 | 100 |
| | 500 | 100 | 100 | 100 |
| | 1000 | 100 | 100 | 100 |
| (12) | 125 | 93 | 93 | 62 |
| | 250 | 94 | 81 | 65 |
| | 500 | 98 | 100 | 70 |
| | 1000 | 100 | 100 | 94 |
| (13) | 125 | 98 | 85 | 80 |
| | 250 | 100 | 97 | 92 |
| | 500 | 100 | 100 | 95 |
| | 1000 | 100 | 100 | 100 |

EXAMPLE 5

With the compounds (1), (2), (5), (8), (12) and (13) and d-allethrin [(RS)-3-allyl-2-methyl-4-oxocyclopent-2-enyl (1R)-cis.trans-chrysanthemate], a bag for protecting grains from the insect pests of 20 cm in height and 13 cm in width was prepared in the same manner as in Example 1.

Separately, d-allethrin was applied to a porous non-woven fabric in the same manner as in Example 1. With the treated non-woven fabric, a bag for protecting grains from the insect pests of the same size as above was prepared in the same manner as in Example 1.

300 Grams of unpolished rice was put in these bags, and the bags were closed air-tight. Thereafter, the bags were put in a (20 cm)³ corrugated cardboard box and stored at room temperature. After 2 weeks, 2 months or 6 months, 100 adults of maize weevil (Sitophilus zeamais) were released in the box and allowed to stand for 1 week. While the adults were allowed to stand, they were fed with a 1% sugar water in absorbent cotton. Thereafter, the mortality of the test insect was determined. The mortality wa calculated by the following equation. The dosage rate of the test compound was about 1,000 mg per square meter of the paper.

$$\text{Mortality of test insects (\%)} = \frac{\text{Number of dead insects}}{\text{total number of test insects}} \times 100$$

The results are shown in Table 4.

TABLE 4

| Test compound | Material of bag | Mortality (%) | | |
|---|---|---|---|---|
| | | 2 weeks | 2 months | 6 months |
| (1) | Kraft paper | 94 | 80 | 62 |
| (2) | " | 91 | 84 | 76 |
| (5) | " | 95 | 92 | 79 |
| (8) | " | 88 | 95 | 65 |

TABLE 4-continued

| Test compound | Material of bag | Mortality (%) | | |
|---|---|---|---|---|
| | | 2 weeks | 2 months | 6 months |
| (12) | " | 89 | 92 | 82 |
| (13) | " | 85 | 89 | 87 |
| d-Allethrin | " | 80 | 55 | 15 |
| d-Allethrin | Porous non-woven cloth | 72 | 40 | 8 |

What is claimed is:

1. A bag for protecting grains from insect pests harmful to stored grains comprising a multi-layer kraft paper laminate comprising (a) one piece of kraft paper treated on one surface with at least one member selected from the group consisting of the following pyrethroid insecticides:

3-phenoxybenzyl chrysanthemate, 3-phenoxybenzyl 3-(2,2-dichlorovinyl)-2,2-dimethylcyclopropanecarboxylate, α-cyano-3-phenoxybenzyl chrysanthemate, 5-benzyl-3-furylmethyl chrysanthemate, α-cyano-3-phenoxybenzyl 2-(4-chlorophenyl)-3-methylbutyrate, α-cyano-3-phenoxybenzyl 2,2,3,3-tetramethylcyclopropanecarboxylate, α-cyano-3-phenoxybenzyl 3-(2,2-dichlorovinyl)-2,2-dimethylcyclopropanecarboxylate, α-cyano-3-phenoxybenzyl 3-(2,2-dibromovinyl)-2,2-dimethylcyclopropanecarboxylate, α-cyano-3-phenoxybenzyl 3-(2-chloro-3,3,3-trifuloro-1-propenyl)-2,2-dimethylcyclopropanecarboxylate, α-cyano-3-phenoxybenzyl 2-(4-difluoromethoxyphenyl)-3-methylbutyrate, α-cyano-4-fluoro-3-phenoxybenzyl 3-(2,2-dichlorovinyl)-2,2-dimethylcyclopropanecarboxylate, 2-(4-ethoxyphenyl)-2-methylpropyl 3-phenoxybenzyl ether and α-cyano-3-phenoxybenzyl 2,2-dimethyl-3-(1,2,2,2-tetrabromoethyl)cyclopropanecarboxylate, and (b) 1 to 5 pieces of kraft paper containing no pyrethroid insecticide, the surface of the former kraft paper treated with the pryethroid insecticide facing the outside.

2. A bag according to claim 1, wherein the content of the pyrethroid insecticide is 10 to 1,000 mg per square meter of the treated kraft paper.

3. A bag according to claim 1, wherein a thin polymer film is inserted between the intermediate layers of the multi-layer kraft paper laminate or the intermediate layer is backed with the polymer film at the innter surface.

4. A method for producing a bag for protecting grains from insect pests harmful to stored grains which comprises treating one piece of kraft paper on one surface with an insecticidal solution containing at least one member selected from the group consisting of the following pyrethroid insecticides:

3-phenoxybenzyl chrysanthemate, 3-phenoxybenzyl 3-(2,2-dichlorovinyl)2,2-dimethylcyclopropanecarboxylate, α-cyano-3-phenoxybenzyl chrysanthemate, 5-benzyl-3-furylmethyl chrysanthemate, α-cyano-3-phenoxybenzyl 2-(4-chlorophenyl)-3-methylbutyrate, α-cyano-3-phenoxybenzyl 2,2,3,3-tetramethylcyclopropanecarboxylate, α-cyano-3-phenoxybenzyl 3-(2,2-dichlorovinyl)-2,2-dimethylcyclopropanecarboxylate,
α-cyano-3-phenoxybenzyl 3-(2,2-dibromovinyl)-2,2-dimethylcyclopropanecarboxylate,
α-cyano-3-phenoxybenzyl 3(2-chloro-3,3,3-trifluoro-1-propenyl)-2,2-dimethylcyclopropanecarboxylate,
α-cyano-3-phenoxybenzyl 2-(4-difluoromethyoxyphenyl)-3-methylbutyrate,
α-cyano-4-fluoro-3-phenoxybenzyl-3-(2,2-dichlorovinyl)-2,2-dimethylcyclopropanecarboxylate,
2-(4-ethoxyphenyl)-2-methylpropyl 3-phenoxybenzyl ether and
α-cyano-3-phenoxybenzyl 2,2-dimethyl-3-(1,2,2,2-tetrabromoethyl)cyclopropanecarboxylate,
  laminating 1 to 5 pieces of untreated kraft paper to which the pyrethroid insecticide is not applied onto the untreated surface of the treated kraft paper, and then forming the resulting kraft paper laminate into a bag so that the surface of the treated kraft paper onto which the pyrethroid insecticide has been applied faces the outside.

5. A method according to claim 4, wherein the insecticidal solution is an oil spray, liquid formulation, water-based emulsifiable concentrate or flowable concentrate.

6. A method for protecting grains from insect pests harmful to stored grains which comprises preserving grains in a bag produced by forming a multi-layer kraft paper laminate comprising one piece of kraft paper onto which has been applied on one surface at least one member selected from the group consisting of the following pyrethroid insecticides:
3-phenoxybenzyl chrysanthemate,
3-phenoxybenzyl 3-(2,2-dichlorovinyl)-2,2-dimethylcyclopropanecarboxylate,
α-cyano-3-phenoxybenzyl chrysanthemate,
5-benzyl-3-furylmethyl chrysanthemate,
α-cyano-3-phenoxybenzyl 2-(4-chlorophenyl)-3-methylbutyrate,
α-cyano-3-phenoxybenzyl 2,2,3,3-tetramethylcyclopropanecarboxylate,
α-cyano-3-phenoxybenzyl 3-(2,2-dichlorovinyl)-2,2-dimethylcyclopropanecarboxylate,
α-cyano-3-phenoxybenzyl 3-(2,2-dibromovinyl)-2,2-dimethylcyclopropanecarboxylate,
α-cyano-3-phenoxybenzyl 3-(2-chloro-3,3,3-trifluoro-1-propenyl)-2,2-dimethylcyclopropanecarboxylate,
α-cyano-3-phenoxybenzyl 2-(4-difluoromethoxyphenyl)-3-methylbutyrate,
α-cyano-4-fluoro-3-phenoxybenzyl-3-(2,2-dichlorovinyl)-2,2-dimethylcyclopropanecarboxylate,
2-(4-ethoxyphenyl)-2-methylpropyl 3-phenoxybenzyl ether and
α-cyano-3-phenoxybenzyl 2,2-dimethyl-3(1,2,2,2-tetrabromoethyl)cyclopropanecarboxylate,
  and 1 to 5 pieces of kraft paper to which the foregoing pyrethroid insecticide is not applied and which are laminated on the treated kraft paper, into a bag so that the surface of the treated kraft paper onto which the pyrethroid insecticide has been applied faces the outside.

7. A method according to claim 6, wherein the amount of the pyrethroide insecticide to be applied is 10 to 1,000 mg per square meter of the treated paper.

8. A method according to claim 6, wherein the thin polymer film is inserted between the intermediate layers of the multi-layer kraft paper laminate or the intermediate layer is backed with the polymer film at the inner surface.

* * * * *